US012614326B2

(12) United States Patent
Wilk

(10) Patent No.: US 12,614,326 B2
(45) Date of Patent: Apr. 28, 2026

(54) METHODS AND SYSTEMS FOR SCATTER AND TAILING CORRECTION

(71) Applicant: GE Precision Healthcare LLC, Wauwatosa, WI (US)

(72) Inventor: Michael Wilk, Haifa (IL)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 427 days.

(21) Appl. No.: 18/311,717

(22) Filed: May 3, 2023

(65) Prior Publication Data

US 2024/0371053 A1     Nov. 7, 2024

(51) Int. Cl.
| | |
|---|---|
| *G06T 11/00* | (2006.01) |
| *A61B 6/42* | (2024.01) |
| *G01T 1/24* | (2006.01) |

(52) U.S. Cl.
CPC .......... *G06T 11/005* (2013.01); *A61B 6/4241* (2013.01); *G01T 1/24* (2013.01); *G06T 2210/41* (2013.01)

(58) Field of Classification Search
None
See application file for complete search history.

(56) References Cited

U.S. PATENT DOCUMENTS

| | | |
|---|---|---|
| 10,302,578 B2 | 5/2019 | Li et al. |
| 2021/0279917 A1* | 9/2021 | Wilk .................... A61B 6/5282 |
| 2024/0100203 A1* | 3/2024 | Bénard ................... A61P 35/00 |

FOREIGN PATENT DOCUMENTS

WO      2019052815 A1     3/2019

OTHER PUBLICATIONS

Iatrou, M. et al., "3D implementation of Scatter Estimation in 3D PET," Proceedings of the 2006 IEEE Nuclear Science Symposium Conference Record, Oct. 29, 2006, San Diego, California, 4 pages.

Kacperski, K. et al., "Iterative deconvolution of simultaneous 99mTc and 201Tl projection data measured on a CdZnTe-based cardiac Spect scanner," Physics in Medicine and Biology, vol. 56, No. 5, Mar. 7, 2011, Available Online Feb. 11, 2011, 25 pages.

Holstensson, M. et al., "Model-based correction for scatter and tailing effects in simultaneous 99mTc and 123I imaging for a CdZnTe cardiac Spect camera," Physics in Medicine and Biology, vol. 60, No. 8, Apr. 21, 2015, Available Online Mar. 24, 2015, 20 pages.

Niimi, T. et al., "Comparative Cardiac Phantom Study Using Tc-99m/I-123 and TI-201/I-123 Tracers with Cadmium-Zinc-Telluride Detector-Based Single-Photon Emission Computed Tomography," Nuclear Medicine and Molecular Imaging, vol. 53, No. 1, Feb. 2019, Available Online Dec. 12, 2018, 7 pages.

* cited by examiner

*Primary Examiner* — Helen Zong

(74) *Attorney, Agent, or Firm* — McCoy Russell LLP

(57)     ABSTRACT

Various methods and systems are provided for a method for nuclear medicine (NM) imaging, comprising, acquiring imaging data with at least two energy windows, pre-processing acquired imaging data to separate distributions of scattered photons and peak photons, performing a main iterative reconstruction to reconstruct a corrected imaging using scatter correction, tailing correction, and/or scatter and tailing correction from distributions of scattered photons and peak photons, and outputting the corrected image.

17 Claims, 10 Drawing Sheets

METHODS AND SYSTEMS FOR SCATTER AND TAILING CORRECTION

FIELD

Embodiments of the subject matter disclosed herein relate to non-invasive diagnostic imaging, and in particular to scatter correction using tailing photons for nuclear medicine (NM) imaging systems.

BACKGROUND

Nuclear medicine (NM) imaging systems, such as positron emission tomography (PET) imaging systems and single photon emission computed tomography (SPECT) imaging systems, include multiple detectors or detector heads for detecting radiation emitted from within a subject in order to image the internal structure of the subject. For example, PET imaging systems acquire data that represent the distribution of positron-emitting nuclides within the body of a patient. When a positron interacts with an electron by annihilation, the entire mass of a positron-electron pair is converted into two 511-keV photons. The photons are emitted in opposite directions along a line of response (LOR). The annihilation photons are detected by detectors that are placed on both sides of the LOR, in a configuration such as a detector ring. Coincidence occurs when these annihilation photons arrive and are detected at the detector elements at the same time. An image is then generated based on the acquired image data that includes the annihilation photon detection information. SPECT imaging systems acquire data that represents a distribution of a radioactive substance introduced into the patient, which may be absorbed in a target organ or area of a body of the patient. The radioactive substance emits photons, which are collimated and detected by a detector subsystem, such as a cadmium zinc telluride (CZT) detector. Detectors of the subsystem may generate output electrical signals from which three dimensional (3D) images can be created, where the 3D images show a distribution of the radioactive substance in and around the target organ or area.

Compton scattering occurs when photons interact with matter, change direction, and lose energy. The detection of such scattered photons causes errors and/or image artifacts. NM imaging systems are typically configured with scatter correction methods to account for Compton scattering.

BRIEF DESCRIPTION

In one embodiment, a method comprises acquiring imaging data with at least two energy windows, pre-processing acquired imaging data to separate distributions of scattered photons and peak photons, performing a main iterative reconstruction to reconstruct a corrected imaging using scatter correction, tailing correction, and/or scatter and tailing correction from distributions of scattered photons and peak photons, and outputting the corrected image.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below:

FIG. 7 shows a set of images illustrating example corrected images of distribution of Lu177 low peak according to an embodiment described herein;

FIG. 9 shows a set of images illustrating example corrected images of distribution of Tc99m according to an embodiment described herein.

DETAILED DESCRIPTION

Figure 1:
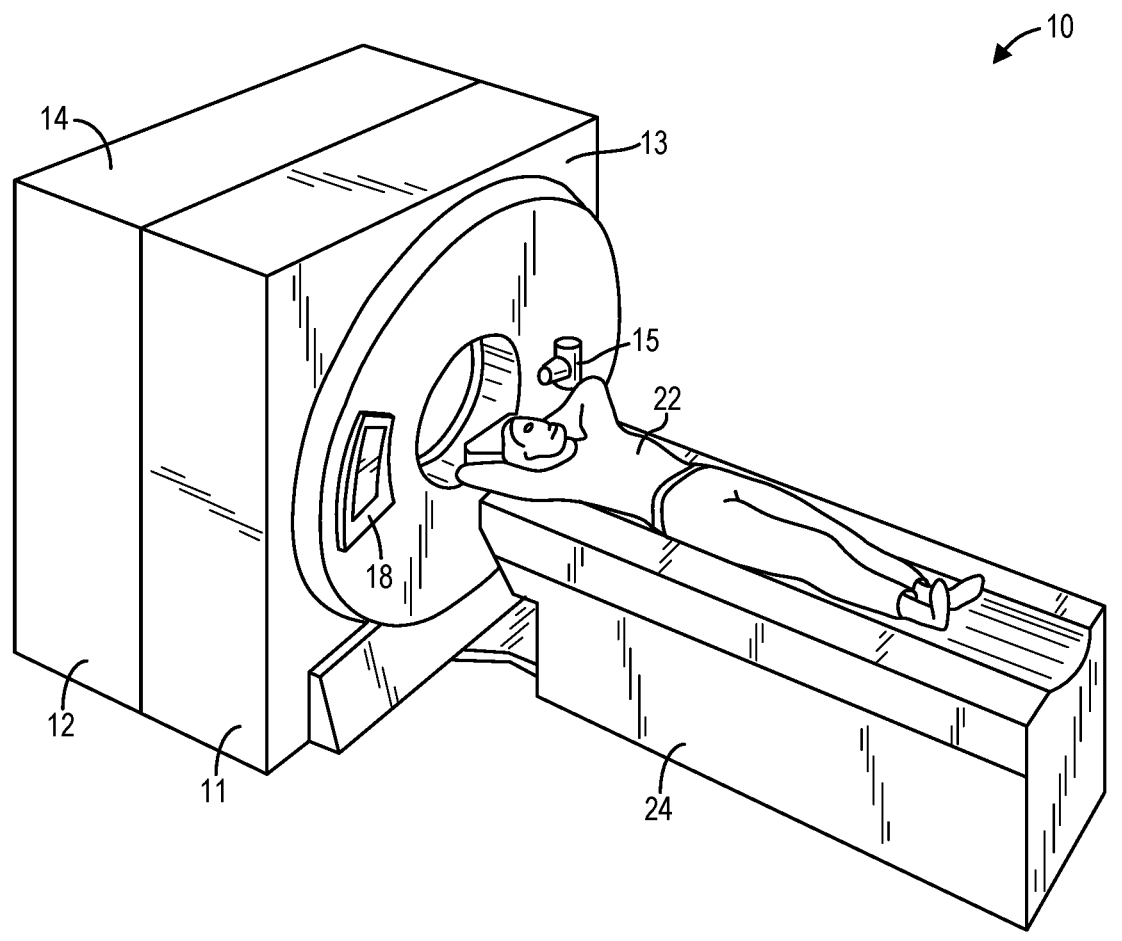
FIG. 1 shows a pictorial view of an exemplary multi-modality imaging system according to an embodiment of the invention.
Figure 2:
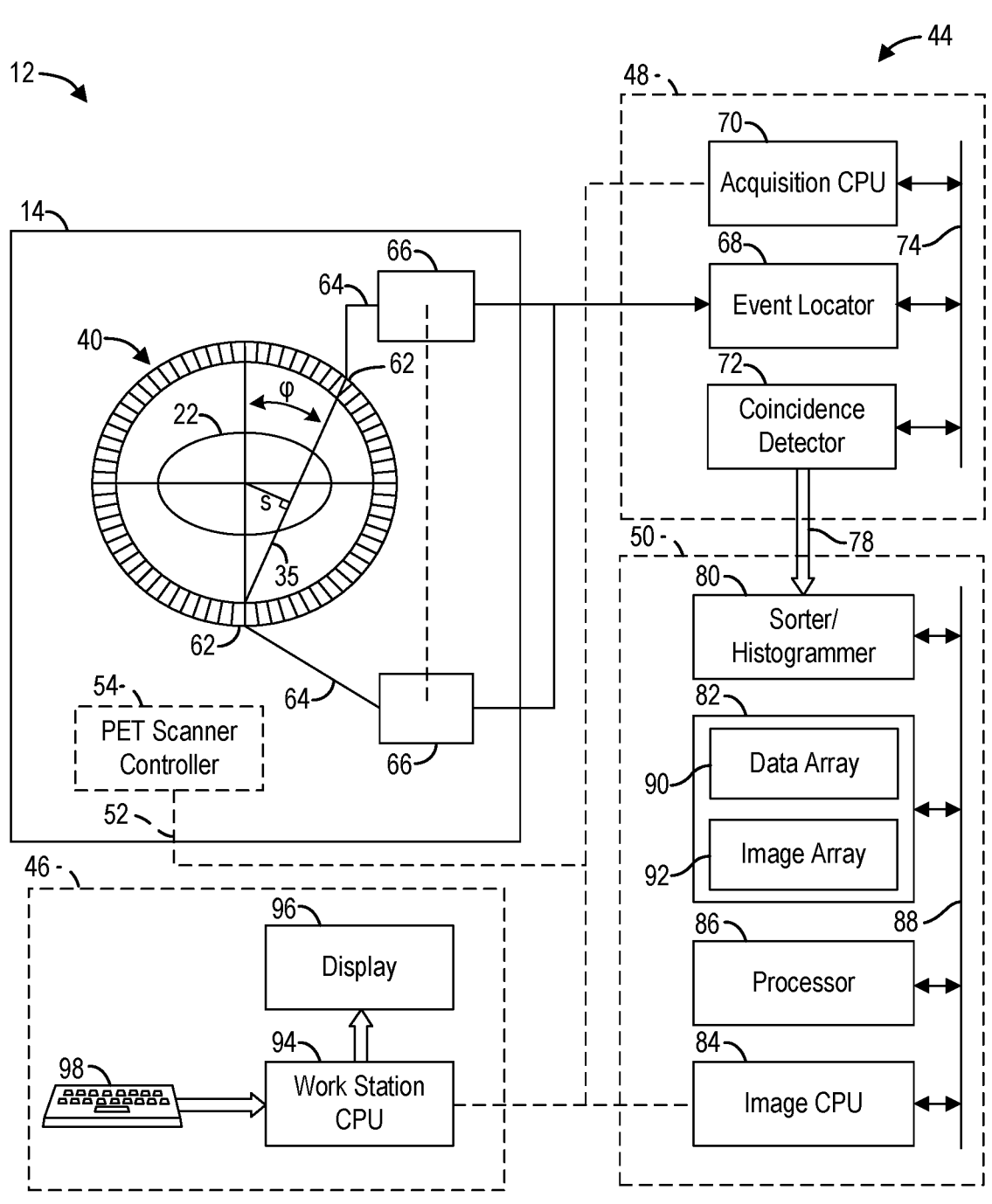
FIG. 2 shows a block schematic diagram of an exemplary imaging system with a detector, according to an embodiment of the invention.
Figure 3:
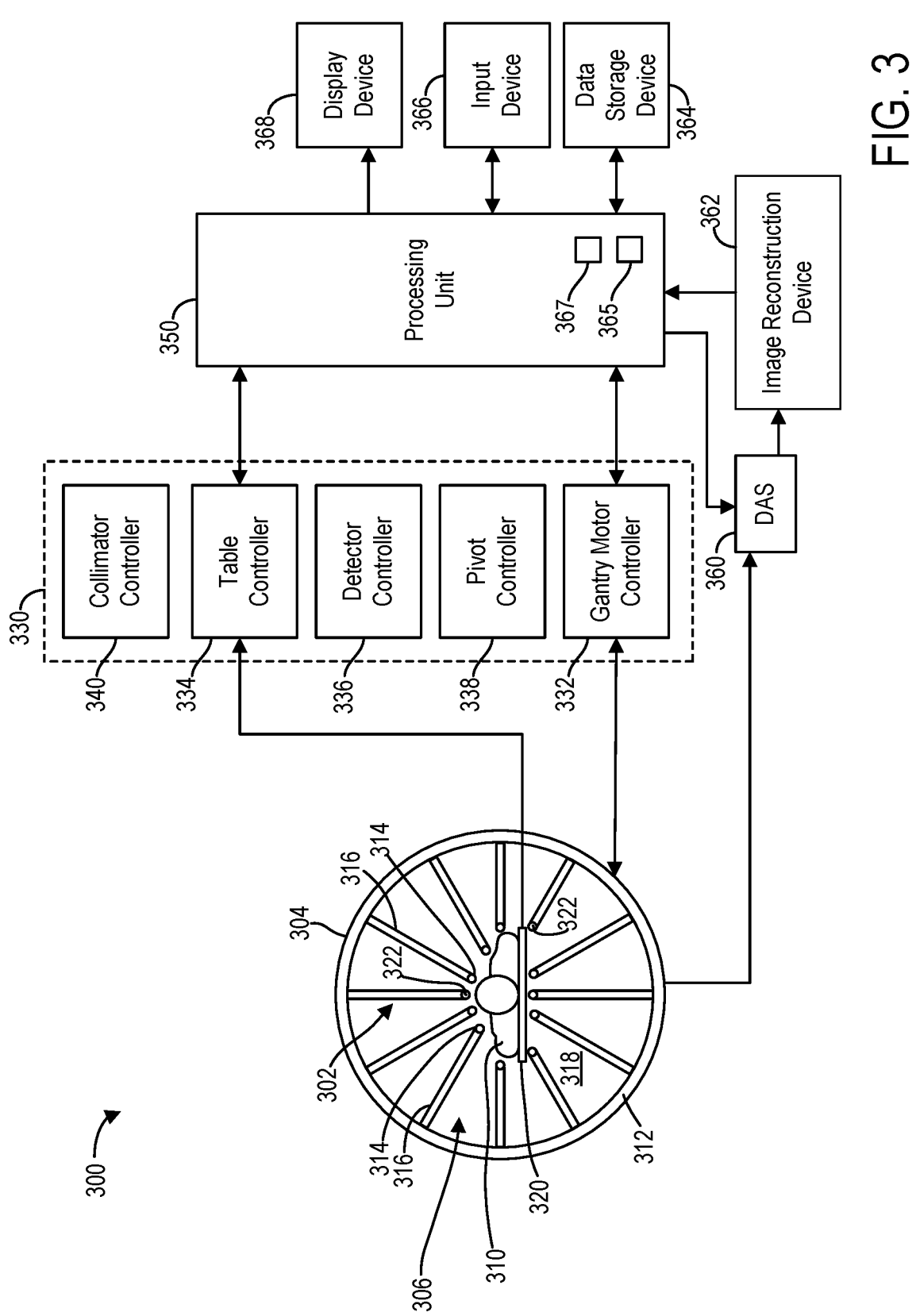
FIG. 3 is a schematic block diagram of a NM imaging system in accordance with an embodiment.
Figure 4:
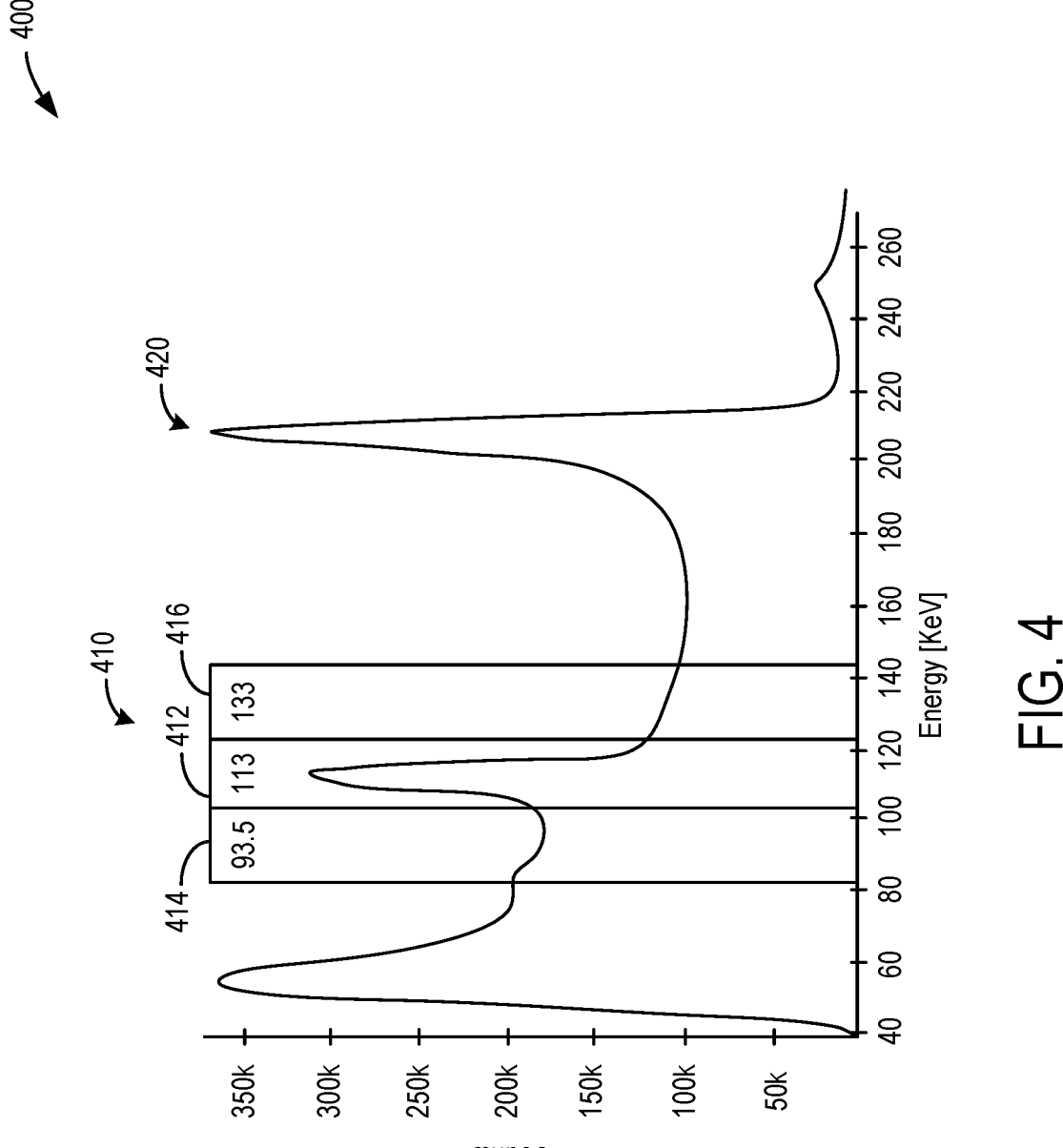
FIG. 4 shows a graph illustrating an example distribution of Lu177 low peak SPECT acquired photon counts, including photopeak, tailed photons, and scattered photons, according to an embodiments of the invention.
Figure 7:
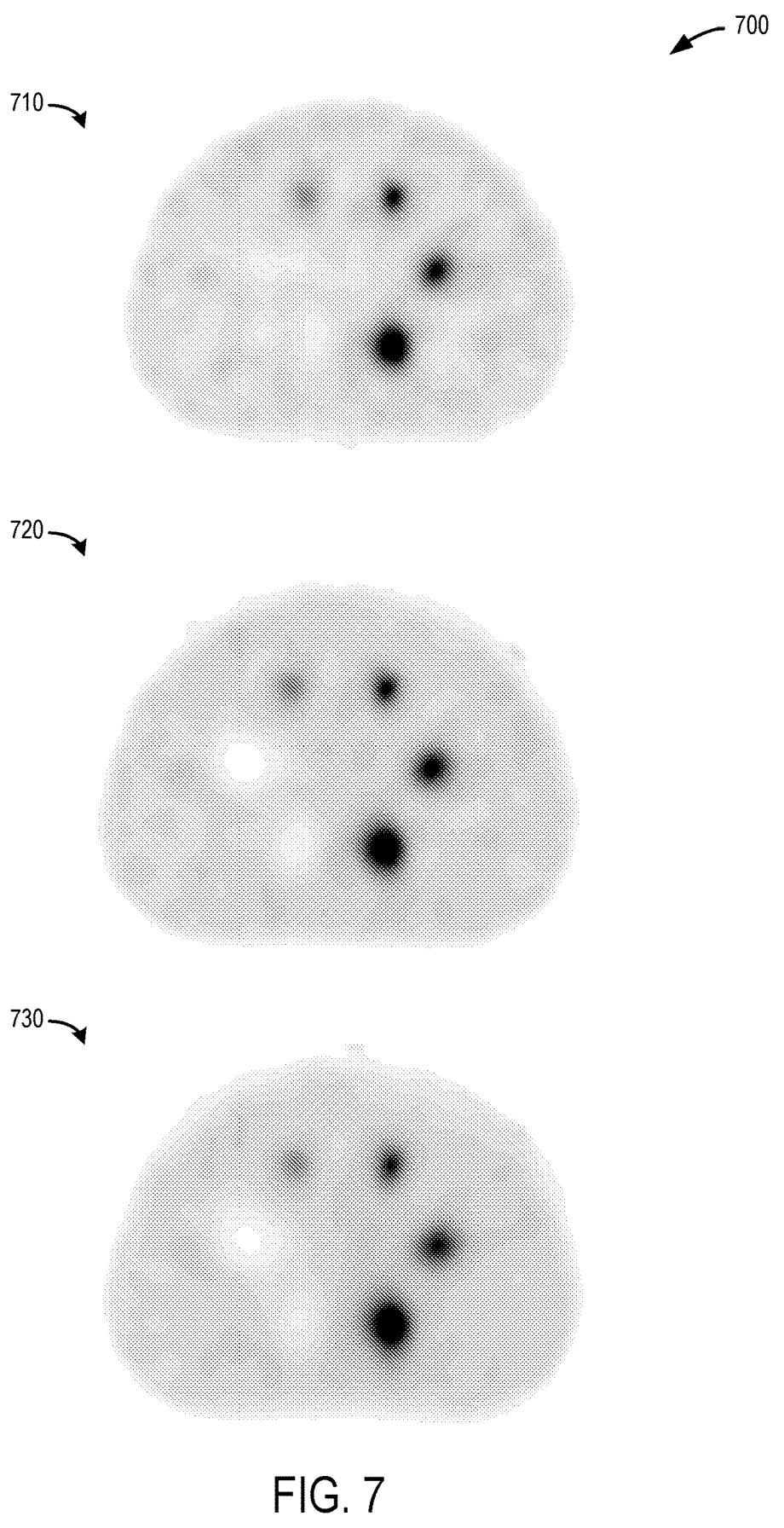
Figure 8:
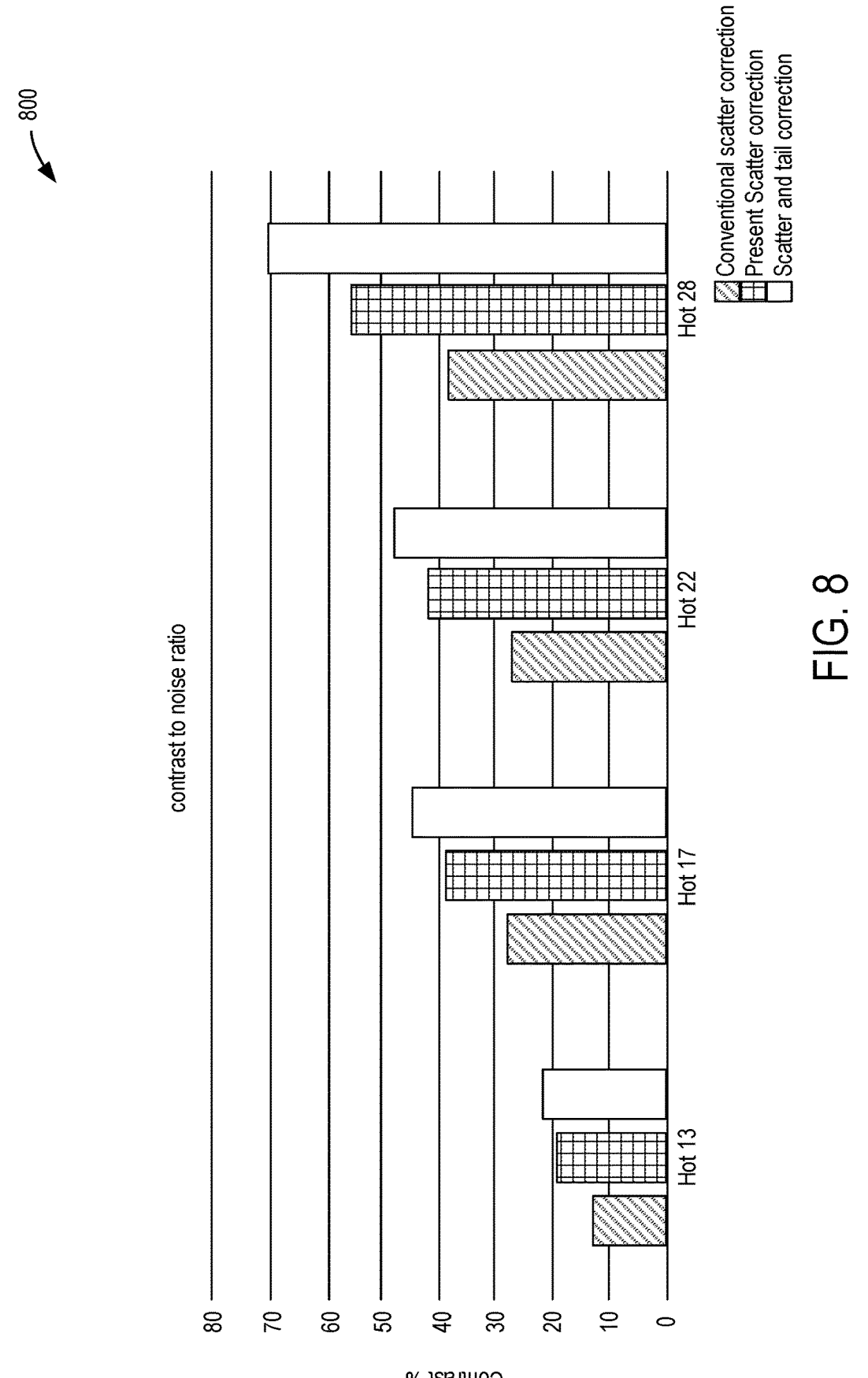
FIG. 8 shows a graph illustrating example contrast to noise ratios for the example scatter images of FIG. 7.
Figure 9:
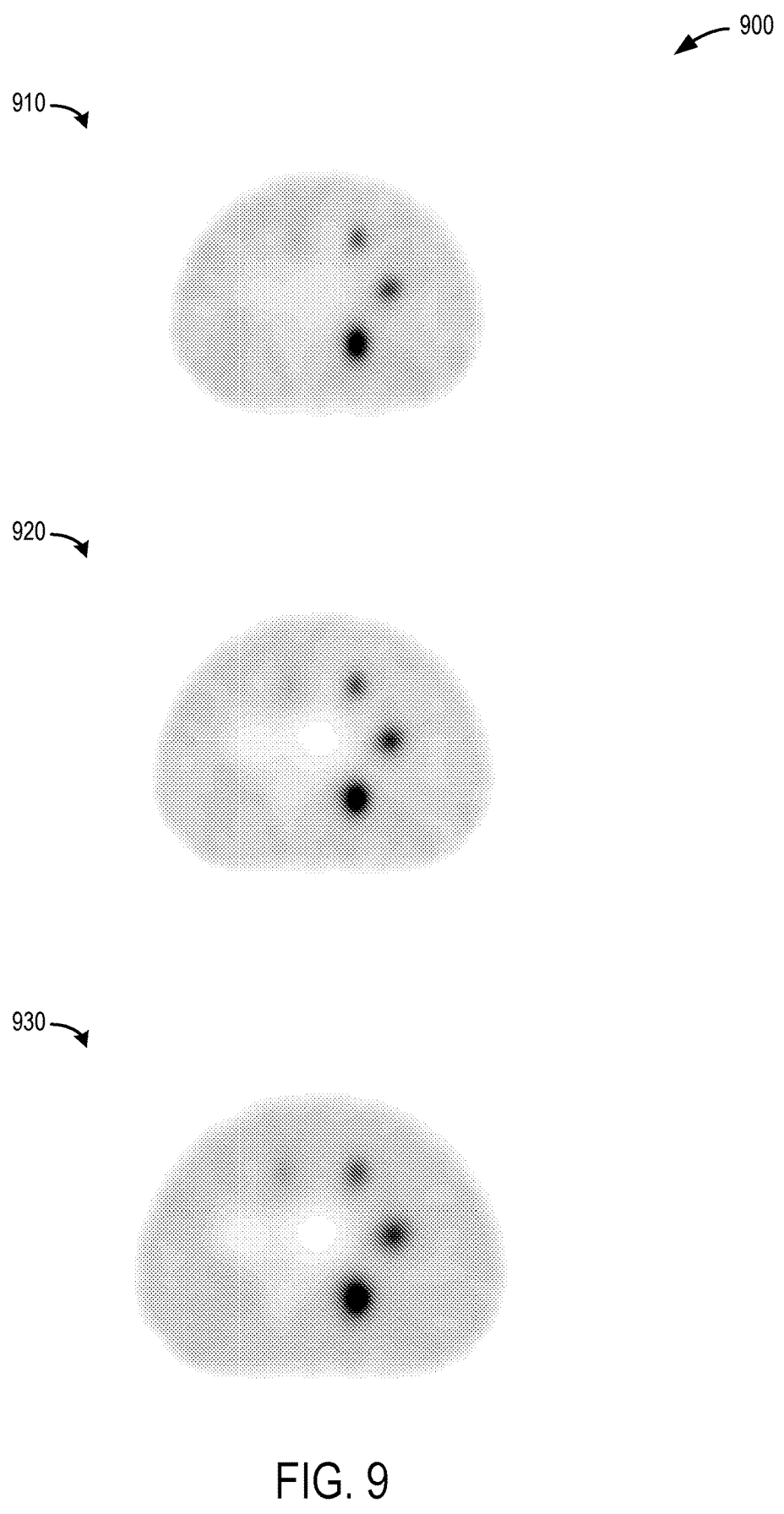
Figure 10:
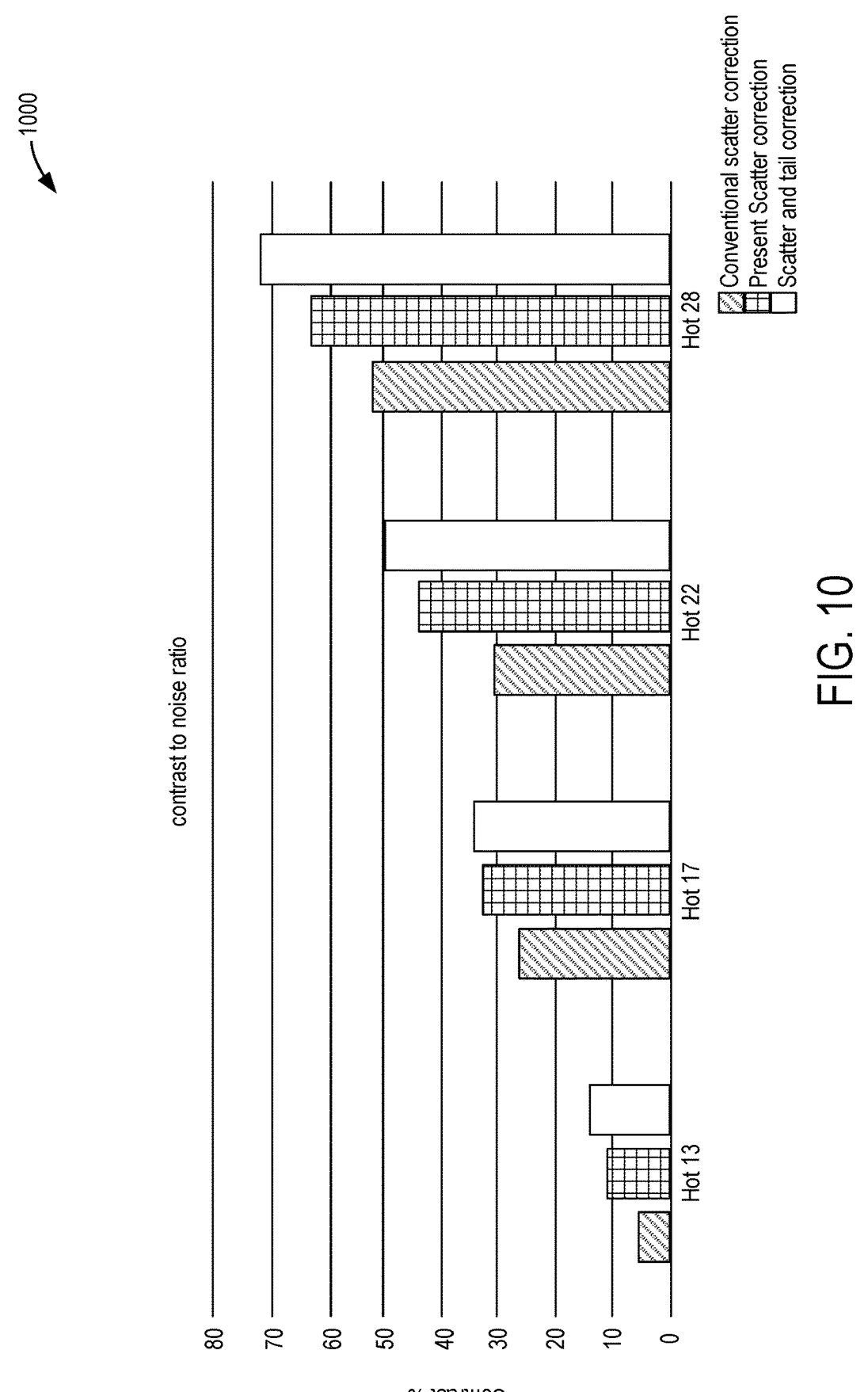
FIG. 10 shows a graph illustrating example contrast to noise ratios for the example scatter images of FIG. 9.

The following description relates to various embodiments of nuclear medicine (NM) imaging. In particular, systems and methods are provided for scatter correction and tailing correction for a NM imaging system, such as a SPECT imaging system or a PET imaging. An example of a PET imaging system that may be used to acquire images processed in accordance with the present techniques is shown in FIGS. 1 and 2. Another example of a NM imaging system that may be used to acquire images processed in accordance with the present techniques, in particular a SPECT imaging system, is shown in FIG. 3. A PET imaging system may be configured with low energy resolution detectors for wide energy window scans while a SPECT imaging system may be configured with CZT detectors which provide an increased energy resolution in comparison to more traditional NaI detectors. However, for systems configured with CZT detectors, the photopeak resolution is often asymmetric due to incomplete charge collection within the detector, resulting in many photopeak events being incorrectly sorted into lower energy bins. This "tailing" effect caused by such incorrectly binned photopeak photons, as depicted in FIG. 4, contaminates the true scatter signal in the lower energy bins, thereby negatively impacting scatter correction methods that rely on estimates of scatter from the spectra. Methods for scatter correction and tailing correction, such as the method shown in FIG. 5, include statistical separation of a distribution of scattered photons and tailing photons based on decomposition of true photopeak photons, scattered photons, and tailing photons acquired in multiple energy windows. The method of FIG. 5 includes reconstructing pure scatter images, shown in FIG. 6, of each of the scatter energy windows to identify respective distributions of scattered photons. FIGS. 7 and 9 show example sets of corrected images which have been corrected using different methods, and FIGS. 8 and 10 show example contrast to noise ratios of the corrected images of FIGS. 7 and 9, respectively.

Various embodiments of the invention provide a multi-modality imaging system 10 as shown in FIGS. 1 and 2. Multi-modality imaging system 10 may be any type of imaging system, for example, different types of medical imaging systems, such as a Positron Emission Tomography (PET), a Single Photon Emission Computed Tomography (SPECT), a Computed Tomography (CT), an ultrasound system, Magnetic Resonance Imaging (MRI), or any other system capable of generating tomographic images. The various embodiments are not limited to multi-modality medical imaging systems, but may be used on a single modality medical imaging system such as a stand-alone PET imaging system or a stand-alone SPECT imaging system, for example. Moreover, the various embodiments are not limited to medical imaging systems for imaging human subjects, but may include veterinary or non-medical systems for imaging non-human objects.

Referring to FIG. 1, the multi-modality imaging system 10 includes a first modality unit 11 and a second modality unit 12. The two modality units enable the multi-modality imaging system 10 to scan an object or patient in the first modality unit 11 using the second modality unit 12. The multi-modality imaging system 10 allows for multiple scans in different modalities to facilitate an increased diagnostic capability over single modality systems. In one embodiment, multi-modality imaging system 10 is a Computed Tomography/Positron Emission Tomography (CT/PET) imaging system, e.g., the first modality unit 11 is a CT imaging system and the second modality unit 12 is a PET imaging system. The CT/PET system is shown as including a gantry 13 representative of a CT imaging system and a gantry 14 that is associated with a PET imaging system. As discussed above, modalities other than CT and PET may be employed with the multi-modality imaging system 10.

The gantry 13 includes an x-ray source 15 that projects a beam of x-rays toward a detector array 18 on the opposite side of the gantry 13. Detector array 18 is formed by a plurality of detector rows (not shown) including a plurality of detector elements which together sense the projected x-rays that pass through a medical patient 22. Each detector element produces an electrical signal that represents the intensity of an impinging x-ray beam and hence allows estimation of the attenuation of the beam as it passes through the patient 22. During a scan to acquire x-ray projection data, gantry 13 and the components mounted thereon rotate about a center of rotation.

FIG. 2 is a block schematic diagram of the second modality unit 12 (e.g., the PET imaging system) illustrated in FIG. 1 in accordance with an embodiment of the present invention. The PET imaging system includes a detector ring assembly 40 including a plurality of detector crystals. The PET imaging system also includes a controller 44, to control normalization, image reconstruction processes and perform calibration. Controller 44 is coupled to an operator workstation 46. Controller 44 includes a data acquisition processor 48 and an image reconstruction processor 50, which are interconnected via a communication link 52. PET imaging system acquires scan data and transmits the data to data acquisition processor 48. The scanning operation is controlled from the operator workstation 46. The data acquired by the data acquisition processor 48 is reconstructed using the image reconstruction processor 50.

The detector ring assembly 40 includes a central opening, in which an object or patient, such as patient 22 may be positioned using, for example, a motorized table 24 (shown in FIG. 1). The motorized table 24 is aligned with the central axis of detector ring assembly 40. This motorized table 24 moves the patient 22 into the central opening of detector ring assembly 40 in response to one or more commands received from the operator workstation 46. A PET scanner controller 54, also referred to as the PET gantry controller, is provided (e.g., mounted) within PET system. The PET scanner controller 54 responds to the commands received from the operator workstation 46 through the communication link 52. Therefore, the scanning operation is controlled from the operator workstation 46 through PET scanner controller 54.

During operation, when a photon collides with a crystal 62 on a detector ring 40, it produces a scintillation event on the crystal. Each photomultiplier tube or photosensor produces an analog signal that is transmitted on communication line 64 when a scintillation event occurs. A set of acquisition circuits 66 is provided to receive these analog signals. Acquisition circuits 66 produce digital signals indicating the three-dimensional (3D) location and total energy of the event. The acquisition circuits 66 also produce an event detection pulse, which indicates the time or moment the scintillation event occurred. These digital signals are transmitted through a communication link, for example, a cable, to an event locator circuit 68 in the data acquisition processor 48.

The data acquisition processor 48 includes the event locator circuit 68, an acquisition CPU 70, and a coincidence detector 72. The data acquisition processor 48 periodically samples the signals produced by the acquisition circuits 66. The acquisition CPU 70 controls communications on a back-plane bus 74 and on the communication link 52. The event locator circuit 68 processes the information regarding each valid event and provides a set of digital numbers or values indicative of the detected event. For example, this information indicates when the event took place and the position of the scintillation crystal 62 that detected the event. An event data packet is communicated to the coincidence detector 72 through the back-plane bus 74. The coincidence detector 72 receives the event data packets from the event locator circuit 68 and determines if any two of the detected events are in coincidence. Coincidence is determined by a number of factors. First, the time markers in each event data packet must be within a predetermined time period, for example, 12.5 nanoseconds, of each other. Second, the line-of-response (LOR) formed by a straight line joining the two detectors that detect the coincidence event should pass through the field of view in the PET imaging system. Events that cannot be paired are discarded. Coincident event pairs are located and recorded as a coincidence data packet that is communicated through a physical communication link 78 to a sorter/histogrammer 80 in the image reconstruction processor 50.

The image reconstruction processor 50 includes the sorter/histogrammer 80. During operation, sorter/histogrammer 80 generates a data structure known as a histogram. A histogram includes a large number of cells, where each cell corresponds to a unique pair of detector crystals in the PET scanner. Because a PET scanner typically includes thousands of detector crystals, the histogram typically includes millions of cells. Each cell of the histogram also stores a count value representing the number of coincidence events detected by the pair of detector crystals for that cell during the scan. At the end of the scan, the data in the histogram is used to reconstruct an image of the patient. The completed histogram containing all the data from the scan is commonly referred to as a "result histogram." The term "histogrammer" generally refers to the components of the scanner, e.g., processor and memory, which carry out the function of creating the histogram.

The image reconstruction processor 50 also includes a memory module 82, an image CPU 84, an array processor 86, and a communication bus 88. During operation, the sorter/histogrammer 80 counts all events occurring along each projection ray and organizes the events into 3D data. This 3D data, or sinogram, is organized in one exemplary embodiment as a data array 90. Data array 90 is stored in the memory module 82. The communication bus 88 is linked to the communication link 52 through the image CPU 84. The image CPU 84 controls communication through communication bus 88. The array processor 86 is also connected to the communication bus 88. The array processor 86 receives data array 90 as an input and reconstructs images in the form of an image array 92. The resulting image array 92 is then stored in memory module 82.

The images stored in the image array 92 are communicated by the image CPU 84 to the operator workstation 46. The operator workstation 46 includes a CPU 94, a display 96, and an input device 98. The CPU 94 connects to communication link 52 and receives inputs, e.g., user commands, from the input device 98. The input device 98 may be, for example, a keyboard, mouse, a touch-screen panel, and/or a voice recognition system, and so on. Through input device 98 and associated control panel switches, the operator can control the operation of the PET imaging system and the positioning of the patient 22 for a scan. Similarly, the operator can control the display of the resulting image on the display 96 and can perform image-enhancement functions using programs executed by the workstation CPU 94.

The detector ring assembly 40 includes a plurality of detector units. The detector unit may include a plurality of detectors, light guides, scintillation crystals and analog application specific integrated chips (ASICs). For example, the detector unit may include twelve SiPM devices, four light guides, 144 scintillation crystals, and two analog ASICs.

As another example, FIG. 3 is a schematic illustration of a NM imaging system such as a SPECT imaging system 300 having a plurality of imaging detectors 302 mounted on a gantry 304. The imaging detectors 302 may be configured to rotate around a fixed pivot. The movement of the imaging detectors 302 is controlled to reduce the likelihood or avoid collision among the moving imaging detectors and/or reduce the likelihood of one imaging detector obstructing the field of view of another imaging detector. For example, the SPECT imaging system 300 in some embodiments provides coordinated swinging or rotating motion of a plurality of imaging detectors 302 or detector heads.

In particular, a plurality of imaging detectors 302 are mounted to a gantry 304 and/or a patient support structure (not shown) (e.g., under a patient table 320), which may define a table support for a patient table 320. In the illustrated embodiment, the imaging detectors 302 are configured as a detector array 306 positioned around the subject 310 (e.g., a patient), as viewed in FIG. 3. The detector array 306 may be coupled directly to the gantry 304, or may be coupled via support members 312 thereto, to allow movement of the entire array 306 relative to the gantry 304 (e.g., rotational movement in the clockwise or counter-clockwise direction as viewed in FIG. 3). Additionally, each of the imaging detectors 302 includes a detector unit 314, at least some of which are mounted to a movable detector carrier 316 (e.g., a support arm or actuator that may be driven by a motor to cause movement thereof) that extends from the gantry 304. In some embodiments, the detector carriers 316 allow movement of the detector units 314 towards and away from the subject 310, such as linearly. Thus, in the illustrated embodiment the detector array 306 is around the subject 310 and may allow linear movement of the detector units 314, such as towards or away from the patient table 320 in one embodiment. However, other configurations and orientations are possible as described herein, as well as different types of movements (e.g., transverse or perpendicular movement relative to the patient table 320). It should be noted that the movable detector carrier 316 may be any type of support that allows movement of the detector units 314 relative to the support member 312 and/or gantry 304, which in various embodiments allows the detector units 314 to move linearly towards and away from the support member 312, such as radially inward and outwards for positioning adjacent the subject 310. For example, as described herein, the detector units 314 may be controlled to move independently of each other towards or away from the subject 310, as well as capable of rotational, pivoting, or tilting movement in some embodiments.

Each of the imaging detectors 302 in various embodiments is smaller than a conventional whole body or general purpose imaging detector. A conventional imaging detector may be large enough to image most or all of a width of a patient's body at one time and may have a diameter of approximately 50 cm or more. In contrast, each of the imaging detectors 302 may include one or more detector units 314 coupled to a respective detector carrier 316 and having dimensions of 4 cm to 20 cm and may be formed of Cadmium Zinc Telluride (CZT) tiles or modules. For example, each of the detector units 314 may be 8×8 cm in size and be composed of a plurality of CZT pixelated modules (not shown). For example, each module may be 4×4 cm in size and have 16×16=256 pixels. In some embodiments, each detector unit 314 includes a plurality of modules, such as an array of 1×7 modules. However, different configurations and array sizes are contemplated including, for example, detector units 314 having multiple rows of modules.

It should be understood that the imaging detectors may be different sizes and/or shapes with respect to each other, such as square, rectangular, circular, or another shape. An actual field of view (FOV) of each of the imaging detectors 302 may be directly proportional to the size and shape of the respective imaging detector.

The gantry 304 may be formed with an aperture 318 (e.g., opening or bore) therethrough as illustrated. The patient table 320 is configured with a support mechanism, such as the patient support structure, to support and carry the subject 310 in one or more of a plurality of viewing positions within the aperture 318 and relative to the imaging detectors 302. Alternatively, the gantry 304 may comprise a plurality of gantry segments (not shown), each of which may independently move a support member 312 or one or more of the imaging detectors 302.

The gantry 304 may also be configured in other shapes, such as a "C", "H", and "L", for example, and may be rotatable about the subject 310. For example, the gantry 304 may be formed as a closed ring or circle, or as an open arc or arch which allows the subject 310 to be easily accessed while imaging and facilitates loading and unloading of the subject 310, as well as reducing claustrophobia in some subjects 310. For example, in some embodiments the gantry 304 may be arc shaped and the support members 312 may be movable along the arc to position the detector units 314 at different locations along the gantry 304. In some embodiments, the detector units 314 may also be independently movable along the gantry 304.

Additional imaging detectors (not shown) may be positioned to form rows of detector arrays or an arc or ring around the subject 310. By positioning multiple imaging detectors 302 at multiple positions with respect to the subject 310, such as along an imaging axis (e.g., head to toe direction of the subject 310), image data specific for a larger FOV may be acquired more quickly.

Each of the imaging detectors 302 has a radiation detection face, which is directed towards the subject 310 or a region of interest within the subject 310. The radiation detection faces may be covered by or have coupled thereto a collimator 322. The actual FOV for each of the imaging detectors 302 may be increased, decreased, or relatively unchanged by the type of collimator 322. In one embodiment, the collimator 322 is a multi-bore collimator, such as a parallel-hole collimator. However, other types of collimators, such as converging or diverging collimators may optionally or alternatively be used. Other examples for the collimator 322 include pinhole, parallel-beam converging, diverging fan-beam, converging or diverging cone-beam, multi-bore converging, multi-bore converging fan-beam, multi-bore converging cone-beam, multi-bore diverging, or other types of collimators.

Optionally, multi-bore collimators may be constructed to be registered with pixels of the detector units 314, which in one embodiment are CZT detectors. However, other materials may be used. Registered collimation may increase spatial resolution by forcing photons going through one bore to be collected primarily by one pixel. Additionally, registered collimation may increase sensitivity and energy response of pixelated detectors as detector area near the edges of a pixel or in between two adjacent pixels may have reduced sensitivity or decreased energy resolution or other performance degradation. Having collimator septa directly above the edges of pixels reduces the chance of a photon impinging at these degraded performance locations, without decreasing the overall probability of a photon passing through the collimator.

A controller unit 330 may control the movement and positioning of the patient table 320, imaging detectors 302, gantry 304, and/or the collimators 322. A range of motion before or during an acquisition, or between different image acquisitions, is set to maintain the actual FOV of each of the imaging detectors 302 directed, for example, towards or "aimed at" a particular area or region of the subject 310 or along the entire subject 310.

The controller unit 330 may have a gantry motor controller 332, table controller 334, detector controller 336, pivot controller 338, and collimator controller 340. The controllers 330, 332, 334, 336, 338, 340 may be automatically commanded by a processing unit 350, manually controlled by an operator, or a combination thereof. The gantry motor controller 332 may move the imaging detectors 302 with respect to the subject 310, for example, individually, in segments or subsets, or simultaneously in a fixed relationship to one another. For example, in some embodiments, the gantry controller 332 may cause the imaging detectors 302 and/or one or more of the support members 312 to rotate about the subject 310, which may include motion of less than or up to 180 degrees (or more).

The table controller 334 may move the patient table 320 to position the subject 310 relative to the imaging detectors 302. The patient table 320 may be moved in up-down directions, in-out directions, and right-left directions, for example. The detector controller 336 may control movement of each of the imaging detectors 302 to move closer to and farther from a surface of the subject 310, such as by controlling translating movement of the detector carriers 316 linearly towards or away from the subject 310 (e.g., sliding or telescoping movement). Optionally, the detector controller 336 may control movement of the detector carriers 316 to allow coordinated movement of the detector array 306.

The pivot controller 338 may control pivoting, rotating, or swinging movement of the detector units 314 at ends of the detector carriers 316, and/or the detector carrier 316. For example, one or more of the detector units 314 or detector carriers 316 may be rotated or swung about at least one axis to view the subject 310 from a plurality of angular orientations. The collimator controller 340 may adjust a position of an adjustable collimator, such as a collimator with adjustable strips (or vanes) or adjustable pinhole(s).

It should be noted that motion of one or more imaging detectors 302 may be in directions other than strictly axially or radially, and optionally, motions in several motion directions may be used. Moreover, the motions of the imaging detectors 302 are coordinated in various embodiments as described herein. Therefore, the term "motion controller" may be used to indicate a collective name for all motion controllers. It should be noted that the various controllers may be combined, for example, the detector controller 336 and pivot controller 338 may be combined to provide the different movements described herein.

Prior to acquiring an image of the subject 310 or a portion of the subject 310, the imaging detectors 302, gantry 304, patient table 320, and/or collimators 322 may be adjusted as discussed in more detail herein, such as to first or initial imaging positions, as well as subsequent imaging positions. The imaging detectors 302 may each be positioned to image a portion of the subject 310. Alternatively, one or more of the imaging detectors 302 may not be used to acquire data, such as the imaging detectors 302 at ends of the detector array 306, which as illustrated in FIG. 3 are in a protracted position towards the subject 310. Positioning may be accomplished manually by the operator and/or automatically, which may include using other images acquired before the current acquisition, such as by another imaging modality such as CT, MRI, X-ray, PET, or ultrasound. After the imaging detectors 302, gantry 304, patient table 320, and/or collimators 322 are positioned, one or more images are acquired by one or more of the imaging detectors 302 being used, which may include pivoting or swinging motion of one or more of the detector units 314, which may pivot, rotate, or swing to different degrees or between different ranges of angles. The image data acquired by each imaging detector 302 may be combined and reconstructed into a composite image, which may comprise two-dimensional (2D) images, a three-dimensional (3D) volume, or a 3D volume over time (4D).

In one embodiment, the imaging detectors 302, gantry 304, patient table 320, and/or collimators 322 remain stationary after being initially positioned. In another embodiment, an effective field of view for one or more of the imaging detectors may be increased by movement such as pivoting, rotating, or swinging one or more of the imaging detectors 302, rotating the detector array 306 with the gantry 304, adjusting one or more of the collimators 322, or moving the patient table 320.

In various embodiments, a data acquisition system (DAS) 360 receives electrical signal data produced by the imaging detectors 302 and converts this data into digital signals for subsequent processing. An image reconstruction device 362 and a data storage device 364 may be provided in addition to the processing unit 350. It should be noted that one or more functions related to one or more of data acquisition, motion control, data processing, and image reconstruction may be accomplished through hardware, software, and/or by shared processing resources, which may be located within or near the imaging system 300, or may be located remotely. Additionally, a user input device 366 may be provided to receive user inputs (e.g., control commands), as well as a display 368 for displaying images.

Additionally, a detector position controller 365 is also provided, which may be implemented in hardware, software, or a combination thereof. For example, as shown in FIG. 3, the detector position controller 365 may form part of or operate in connection with the processing unit 350. In some embodiments, the detector position controller 365 may be a module that operates to control the movement of the imaging detectors 302, including the detector units 314, such that coordinated or synchronized movement is provided as described herein. It should be noted that movement of a plurality of the imaging detectors 302 and/or detector units 314 may be performed at the same time (e.g., simultaneously or concurrently) or at different times (e.g., sequentially or step-wise, such as back and forth between two detector units 314). It also should be understood that when referring to a detector head, such a detector head may include one or multiple detector modules.

As mentioned hereinabove, Compton scattering occurs when one or both annihilation photons interact with matter (e.g., the patient 22 or the subject 310), change direction, and lose energy. The detection of such scattered photons causes errors and/or image artifacts. An NM imaging system such as the PET imaging system or the SPECT imaging system 300 may therefore be configured to perform scatter correction to reduce errors or image artifacts caused by scattered photons. Scatter correction may be based on measurements of scattered photons or scatter simulations based on emission and attenuation information. For example, one approach to scatter correction is based on the use of multiple energy windows, wherein the information from other windows is used to estimate the scatter within the peak window, and the estimated scatter is subtracted from the peak window. This approach works relatively well for NaI detectors with a modest 10% energy resolution, for example. However, for CZT gamma cameras which offer significantly increased energy resolution in comparison to traditional NaI detectors, the photopeak resolution is often asymmetric due to incomplete charge collection within the detector, resulting in many photopeak events being incorrectly sorted into lower energy bins. This "tailing" effect caused by such incorrectly binned photopeak photons contaminates the true scatter signal in the lower energy bins, thereby negatively impacting scatter correction methods such as the multiple energy window technique mentioned hereinabove that rely on estimates of scatter from the spectra.

As described further herein, systems and methods are provided for scatter and tailing correction based on a decomposition of photopeak photons (e.g., true photopeak photons and tailing photons), and scattered photons acquired in two or more energy windows. For example, the two or more energy windows may comprise a peak window having primary gamma photon energy, and at least one scatter window comprising scattered photon energy. As an illustrative example of how photopeak photons and scattered photons may be distributed over a range of energies and thus decomposed as described further herein, FIG. 4 shows a graph 400 illustrating data acquired or measured with CZT detectors of a SPECT imaging system (e.g., the SPECT imaging system 300 of FIG. 3) during a scan according to an embodiment of the invention. Graph 400 includes a plot of the total distribution of photon counts, including both scattered photons and photopeak photons. A total photon count increases along the ordinate of the graph 400, and an energy increases along the abscissa. The methods and systems of the present disclosure are demonstrated herein using Lu177 low peak (113 KeV) imaging with three energy windows, however the methods and systems may be applied to any isotopes with at least two energy windows, where a scatter window is below (e.g., lower energy) than a peak window. For example, the methods and systems described herein may be applied for Tc99m, as described with respect to FIGS. 9-10, or Lu177 high peak imaging, where each of Tc99m and Lu177 high peak imaging include two windows: a peak window and a scatter window below the peak window.

The total distribution of graph 400 clearly illustrates a so-called photopeak 410 comprising primary gamma photon energy, which comprises 113 KeV in the example, but may comprise a different energy in other examples, depending on the radionuclide(s). The photopeak 410 is referred to herein as a low peak projection of Lu177. The total distribution of photon counts also includes a high peak 420, which comprises 208 KeV, and is characteristic of the radionuclide Lu177 used in the scan. In the example described herein, the photopeak 410 is divided into three energy windows, including a peak window 412 around 113 KeV and two scatter windows: a low scatter window 414 below the peak window 412, and a high scatter window 416 above the peak window 412, with respect to energy magnitude. The peak window 412 includes a range of energies around the photopeak energy, the low scatter window 414 includes a range of energies displaced away from the photopeak energy such that the range of energies for the low scatter window 414 does not overlap with the range of energies for the peak window 412. The high scatter window 416 may include a range of energies displaced away from photopeak energies of the peak window 412 and the low scatter window 414 such that the range of energies for the high scatter window 416 does not overlap with the range of energies for the peak window 412 or of the low scatter window 414.

Within each of the three energy windows are three types of photon distributions: peak photons of the low peak (e.g., the photopeak 410), scattered photons from the high peak 420, and scattered photons from the low peak. Distribution of peak photons in the low peak is the same as that in the high peak 420 and the same as a distribution of tailing photons. The methods described herein with respect to FIG. 5 operate under the assumption that the distribution of peak photons is the same in all three energy windows (e.g., the low scatter window 414, the peak window 412, and the high scatter window 416). A remaining amount of photons in each energy window (e.g., non-peak photons) comprise "scatter", which is composed of scattered photons from the high 208 KeV and low 113 KeV peaks of Lu177. In the low scatter window 414, the peak window 412, and the high scatter window 416, un-scattered tailed photons are from the high Lu177 peak (e.g., the high peak 420). Additionally, the low scatter window 414 includes un-scattered tailed photons from the low Lu177 peak (e.g., the photopeak 410). To match spatial distribution, as further described herein, the method includes convolving reconstructed images of the high scatter window 416 and the low scatter window 414 with three dimensional (3D) Gaussian kernel.

Figure 5:
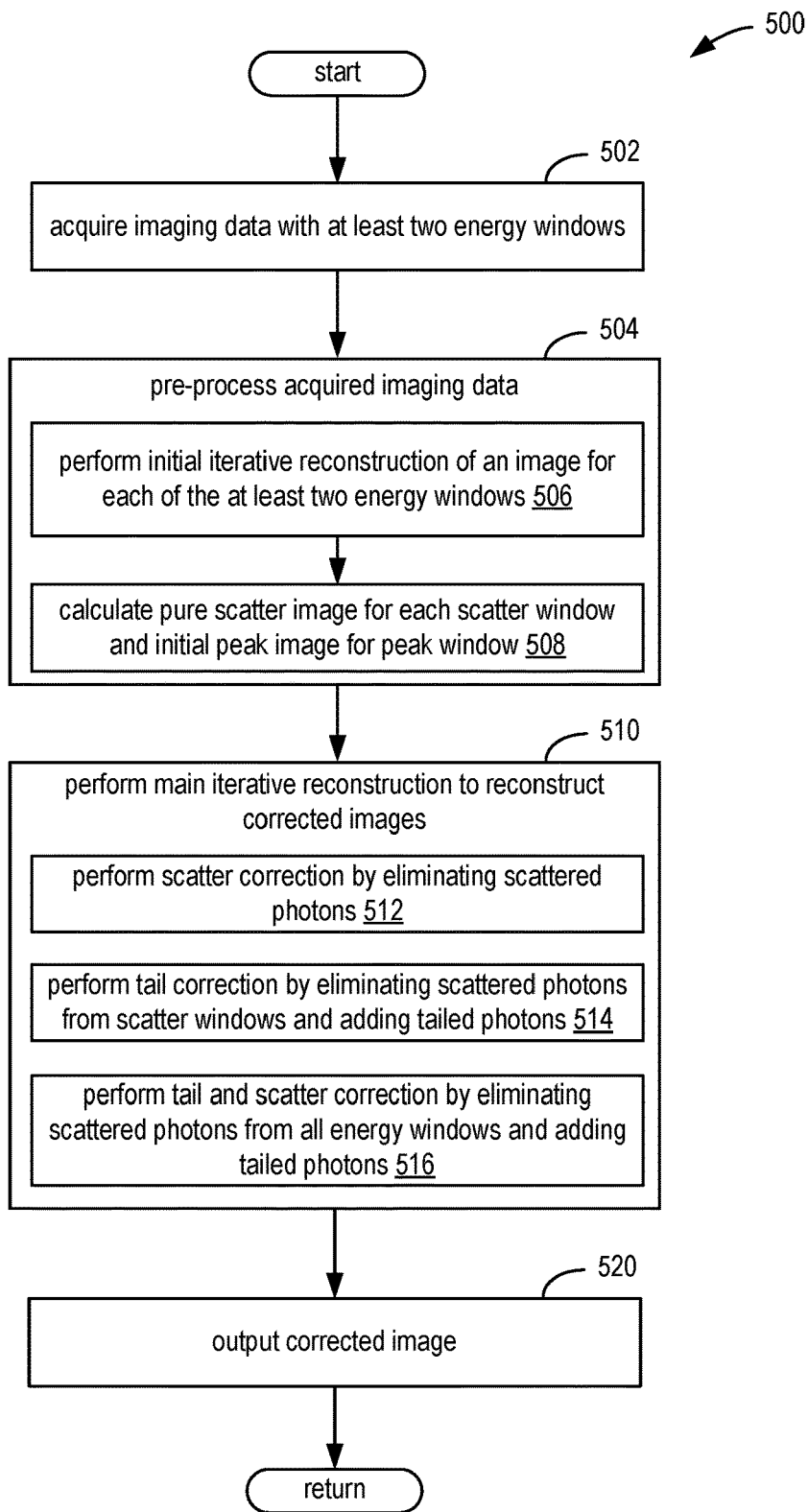
FIG. 5 shows a high-level flow chart illustrating an example method for scatter correction and tailing correction according to an embodiment of the invention.

Imaging data may be corrected for one or more of scatter photons distributions and utilization of tailing photons by statistical decomposition of scattered and primary photon distribution using data from the at least two energy windows. FIG. 5 illustrates a method 500 for statistical decomposition of photon distribution with respect to the example case of Lu177 low peak (e.g., the photopeak 410 of FIG. 4) and the respective three energy windows (e.g., the low scatter window 414, the peak window 412, and the high scatter window 416). As described above, the method 500 may be applied to any imaging data captured using an isotope having at least two energy windows (e.g., a peak energy window and at least one scatter window having less energy than the peak energy window), without departing from the scope of the present disclosure. Applying the method 500 as described herein in the projection space may result in an increased noise level, compared to photons distribution decomposition in the image domain. Thus, the method 500 is described with respect to image domain and projection space, the results of which may be desired in different scenarios.

Method 500 is described with regard to the systems and components of FIGS. 1-3, though it should be appreciated that the method 500 may be implemented with other systems and components without departing from the scope of the present disclosure. Method 500 may be implemented as executable instructions in memory, such as non-transitory memory of the memory module 82, and executed by one or more processors such as the acquisition CPU 70, the image CPU 84, and the array processor 86, as an illustrative and non-limiting example. As another illustrative and non-limiting example, method 500 may be implemented as executable instructions in memory, such as non-transitory memory of the data storage device 364, and executed by one or more processors such as the processing unit 350 and/or the image reconstruction device 362.

At 502, the method 500 includes acquiring imaging data with at least two energy windows. In the example described herein, the imaging data acquired at 502 includes projections of the three energy windows shown in FIG. 4. Method 500 may acquire the imaging data in accordance with a nuclear medicine imaging protocol such as a single-photon emission computed tomography (SPECT) imaging protocol or a positron emission tomography (PET) imaging protocol. In other examples, acquiring imaging data may include requesting and/or retrieving stored imaging data, such as imaging data captured using a nuclear medicine imaging protocol and stored in memory (e.g., the data storage device 364 of FIG. 3, the memory module 82 of FIG. 2).

At 504, the method 500 includes pre-processing acquired imaging data. Pre-processing acquired imaging data as described herein prepares the imaging data to be scatter corrected, tailing corrected, or scatter and tailing corrected. At 506, the method 500 includes performing an initial iterative reconstruction of images from each energy window. The same iterative algorithm may be used to reconstruct each energy window, including the same limited number of iterations. In the example of FIG. 4, three images are reconstructed with each of the three images corresponding to one of the three energy windows.

At 508, the method 500 includes calculating a pure scatter image for each scatter window, and an initial peak image for the peak window. In the example of FIG. 4, the method 500 calculates a pure low scatter image and a pure high scatter image. Each of the pure low scatter image, the pure high scatter image, and the initial peak image are calculated by solving a first system of equations (1), which represents data acquired in each of the three energy windows:

$$HW = k_1 * P + k_2 * SH \tag{1}$$

$$PW = P + k_3 * SL + k_4 * HW$$

$$LW = k_5 * P + SL + k_6 * HW.$$

A total amount of photons in the high scatter window 416 (HW), a total amount of photons in the low scatter window 414 (LW), and a total amount of photons in the peak window 412 (PW) are each weighted sums of photopeak photons (P), scattered photons from the photopeak 410 (SL), and scattered photons from the high peak 420 (SH). Weights $k_i$ of each type of photon distribution in the energy windows are defined by system calibration with and without scattering media and are scaled to adjust a respective energy windows width. Calibration with scattering media provides an estimated fraction of scattered photons, and calibration without scattering media provides an estimated fraction of tail. The solution to the first system of equations (1) is shown in equation (2):

$$\begin{pmatrix} P \\ SH \\ SL \end{pmatrix} = inv(A) * \begin{pmatrix} HW \\ PW \\ LW \end{pmatrix}, \tag{2}$$

where A is defined as shown in equation (3):

$$A = \begin{pmatrix} k_1 & k_2 & 0 \\ (1 + k_4 * k_1) & k_4 * k_2 & k_3 \\ (k_5 + k_6 * k_1) & k_6 * k_2 & 1 \end{pmatrix} \tag{3}$$

Figure 6:
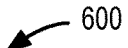
FIG. 6 shows a set of images illustrating example pure scatter images, according to an embodiment of the invention.
Figure 6:
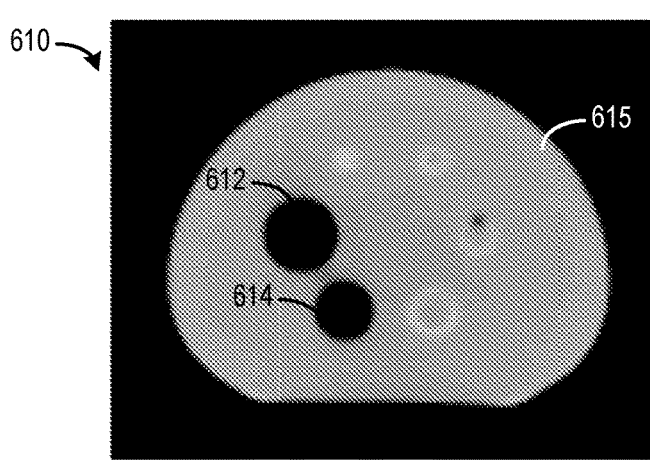
Figure 6:
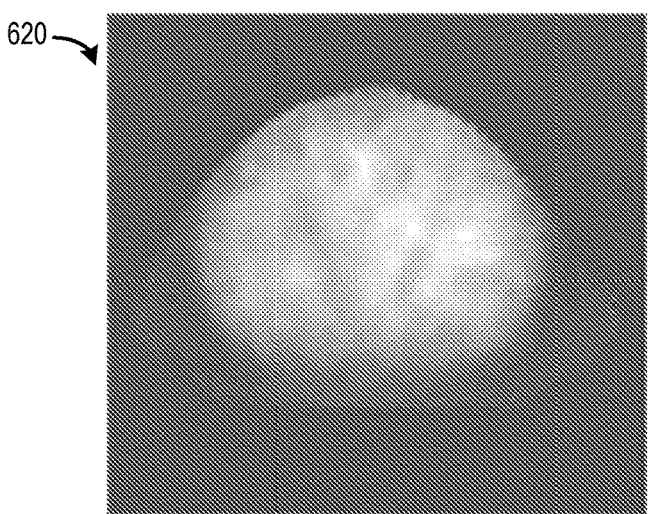
Figure 6:
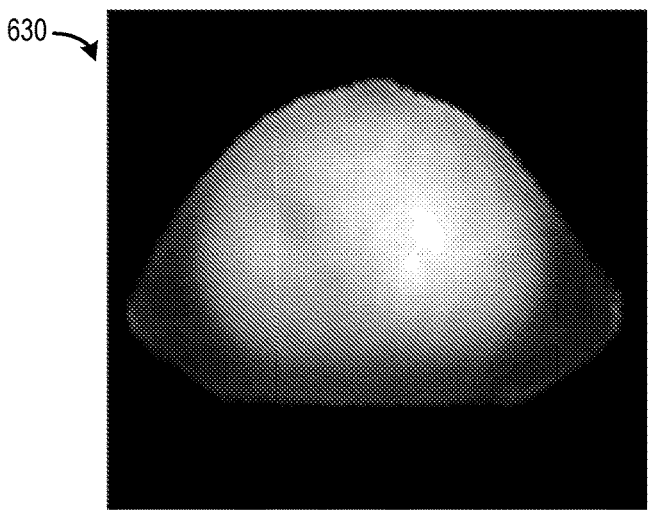

Turning briefly to FIG. 6, examples of a pure low scatter image and a pure high scatter image are shown. FIG. 6 includes a set of images 600 illustrating example pure scatter images, such as may be generated by solving the first system of equations (1) according to the method 500, compared to a phantom. A CT transaxial image 610 shows an image of a National Electrical Manufacturers Association (NEMA) International Electrotechnical Commission (IEC) phantom 615 which adheres to NEMA 2018 definitions with the absence of a lung insert and where two spheres, a first sphere 612 and a second sphere 614, are filled with air instead of water. The phantom 615 was filled with Lu177 and the CT transaxial image 610 was acquired with a CZT camera, such that the image may include scattered and tailed photopeak photons. Each of a pure low scatter image 620 and a pure high scatter image 630 are acquired of the same object (e.g., the phantom 615) using a nuclear medicine scan (e.g., a PET or SPECT scan, as described above) and are reconstructed with a same technique (e.g., the method 500). As described herein with respect to FIG. 5 and further described with respect to FIGS. 7-8, the pure low scatter image 620 and the pure high scatter image 630 include only scatter photons from the photopeak 410 and the high peak 420, respectively, and do not include tailed photons. The pure low scatter image 620 and the pure high scatter image 630 are used for correction via an iterative reconstruction process, as further described herein.

Returning to FIG. 5, at 510, the method 500 includes performing a main iterative reconstruction to reconstruct corrected images. For example, correcting for one or more of scatter photons and tailing photons is performed during the main iterative reconstruction. On each iteration of the reconstruction process, a forward projection step creates projections from the current image. The projections are compared to acquired projections (e.g., peak window projections or the sum of peak, low and high scatter windows projections), and a difference therebetween is backprojected to create an update for the image. The main iterative reconstruction may be performed according to different parameters and using different data depending on a desired type of correction.

At 512, performing the main iterative reconstruction includes performing scatter correction by eliminating scattered photons. Scatter correction is conventionally performed to eliminate scattered photons from a reconstructed image. In some methods, scatter correction is performed by subtracting scattered projections from peak projections during iterative reconstruction. However, this may increase noise in a resulting reconstructed image.

Herein, scatter correction may be performed by adding pre-calculated scatter to projections created during an iterative reconstruction process. For example, pre-calculated scatter projections may be added to a current iteration forward projection. In another example, scatter correction is performed by adding a pre-calculated pure scatter image to a current iteration image before forward projection. For example, the pure low scatter image 620 and the pure high scatter image 630 are added to the initial peak image generated as part of operation 504. On each iteration, scatter is added (e.g., as a scatter image) to an estimated image to forward project the reconstructed image. Following addition of scatter, calculated projections which include scatter (e.g., adding pre-calculate pure scatter image to current iteration image) are compared to acquired projections which include scatter (e.g., FIG. 4), and the comparison provides for eliminating the scatter from the reconstructed image. A difference in images provides a reconstructed image without scatter, thus eliminating scatter photons from the peak window. This method produces the same result as 'scatter subtraction' where scattered photons are subtracted from peak projections, however the method described above preserves an increased amount of noise in the reconstructed image compared to scatter subtraction.

For example, at 512, performing scatter correction includes using peak window acquisition projection data for reconstruction. For correction of scatter at each iteration of the reconstruction process, scatter from SL and SH are added to calculated forward projections, each having respective weights. As described in the PW equation of the first system of equations (1), the peak window acquisition projection data is composed of photopeak photon data (P) and weighted SL and SH data. The correction may be performed in the reconstructed image domain or in projection space using the weighted SL and SH data from the PW equation. In the example of FIG. 4, weights A(2,2) and A(3,2) define weights of scatter portions in the peak window 412, and may be used to weight SH and SL values, respectively, as shown in equation (4):

$$A(2, 2) * SH + A(3, 2) * SL. \qquad (4)$$

Tailing correction may be performed with or without scatter correction. Tailing correction includes adding tailed photons (e.g., from low scatter window and high scatter windows) to peak photons. This is done by combining energy windows. However, combining energy windows as is (e.g., as collected data including scattered photons) results in smeared images. Thus, tailing correction includes separation of scattered photons from the imaging data. A tailing corrected image may be reconstructed from a sum of all three windows. For example, the combinations of photon distributions in the three energy windows as described in the first system of equations (1) may be rewritten as a second system of equations (5):

$$
\begin{aligned}
k_1 & * P + k_2 & * SH + & \ 0 & * SL & = HW & (5)\\
(1 + k_4 * k_1) & * P + k_2 * k_4 & * SH + & \ k_3 & * SL & = PW \\
(k_5 + k_6 * k_1) & * P + k_2 * k_6 & * SH + & \ 1 & * SL & = LW.
\end{aligned}
$$

A sum of all three equations of the second system of equations provides the sum of projections from all energy windows. Using a wide energy window (e.g., spanning all three energy window ranges from the low scatter window 414 to the high scatter window 416) and correction data for scatter provides an addition of the tailed photons to the resulting reconstructed image, compared to an image reconstructed from only the peak energy window (e.g., scatter correction at operation 512). Combination of both scatter and tailing correction may result in a physically quantitative accurate image having increased statistics and less noise, compared to an imaging which is scatter corrected and not tail corrected.

At 514, performing the main iterative reconstruction includes performing tail correction by eliminating scattered photons from the scatter windows and adding tailing photons. Tail correction may be desirable for scans having few photon counts, where it is desirable to increase statistics. Scatter is eliminated from each of the one or more scatter windows (e.g., the high scatter window 416 and the low scatter window 414), and scatter is not removed from the peak window (e.g., the peak window 412). Following removal of scatter, the at least two windows (e.g., scatter window and peak window) are combined into a single, wide energy window. In projection space, correction is performed by adding the weighted pre-calculated scatter projections created from the pure low and pure high scatter images to calculated projections from the current iteration image before comparing calculated projections with acquired projections (the sum of projections acquired in the peak window, low scatter window, and high scatter window). In the reconstructed image domain, correction is performed by adding the pure low and high scatter images to the iteration image before forward projection prior to comparison of calculated projections and acquired projections. Weights for SH and SL which are added to the calculated projections (or images) are as shown in equation 6 for the example of FIG. 4:

$$[A(2, 1) + A(2, 3)] * SH + [A(3, 1) + A(3, 3)] * SL. \qquad (6)$$

The tail correction method thus adds tailed photons to the wide energy window. However, scattered photons are still present in the peak window portion of the wide energy window, thus the resulting reconstructed image is not considered to be scatter corrected. Tailing correction as described herein provides an image with increased statistics than a non-tailing corrected image. Tailing corrected image may be used for visual diagnostics but not quantification.

At 516, performing the main iterative reconstruction includes performing scatter and tailing correction by eliminating scattered photons from all energy windows and adding tailing photons. Scattered photons are eliminated from the peak window as well as the scatter window(s) (e.g., the high scatter window and the low scatter window). In projection space, scatter and tailing correction is performed by adding the weighted scatter projections to calculated projections before comparing calculated projections with acquired projections (e.g., the sum of projections acquired in the peak window, the low scatter window, and the high scatter window). In the reconstructed image domain, correction is performed by adding pure scatter images to the iteration image before forward projection, prior to comparison of calculated projections and acquired projections. Scatter in the peak window is also corrected during scatter and tailing correction. Weights for SH and SL, including the portion of these scatter distributions in the peak window, which are added to the calculated projections (or images) are as shown in equation 7 for the example of FIG. 4:

$$[(A(2, 1) + A(2, 2) + A(2, 3)] * SH + [(A(3, 1) + A(3, 2) + A(3, 3)] * SL. \quad (7)$$

Scatter and tailing corrected images are quantitative with increased statistics, which can be used for quantification (e.g., used to assist diagnosis).

Following reconstruction of a corrected image (e.g., scatter correction, tailing correction, or scatter and tailing correction), the corrected image may be output at 520. For example, the corrected image may be output for display, such as on a display (e.g., the display 96 of FIG. 2), and/or storage, such as in a memory (e.g., the memory module 82 of FIG. 2).

FIG. 7 shows a set of images 700 illustrating example corrected images with at least one of scatter correction and tailing correction according to conventional methods or an embodiment of the invention. Each of the set of images 700 are acquired of a same subject (e.g., a same phantom, such as the phantom 615 of FIG. 6) using a CZT detector, and are reconstructed with a same technique from a same energy window (e.g., the Lu177 low peak (113 KeV)). In the set of images 700, white regions illustrate regions with no activity while shaded regions indicate regions with activity.

In particular, the set of images 700 includes a first scatter-corrected image 710 which is reconstructed using a conventional scatter correction method. The set of images 700 also includes a second scatter-corrected image 720 which is reconstructed using reconstruction methods—as described with respect to operation 512 of the method 500. Compared to the first scatter-corrected image 710, the second scatter-corrected image 720 clearly shows two regions of inactivity (white) as well as four regions of activity (black). Methods used to scatter correct the first scatter-corrected image 710 may be sufficient for scatter correcting data captured using a NaI detector, and are insufficient for scatter correcting data captured using a CZT detector, as shown in FIG. 7.

The set of images 700 further includes a scatter and tailing corrected image 730 which is reconstructed and corrected using methods described with respect to operation 516 of the method 500. Like the second scatter-corrected image 720, the scatter and tailing corrected image 730 clearly shows two regions of inactivity (white) as well as four regions of activity (black). Additionally, a background of the scatter and tailing corrected image 730 has less noise compared to the second scatter-corrected image 720, due to the addition of tailing photons and thus an increase in statistics, enabling the scatter and tailing corrected image 730 to be a more quantitatively accurate image, compared to the second scatter-corrected image 720.

FIG. 8 shows a graph 800 illustrating example contrast to noise ratios of the set of images of FIG. 7. In particular, the graph 800 depicts a contrast to noise ratio of each hot sphere of the phantom 615 for images reconstructed and corrected using conventional scatter correction (diagonal line infill, the first scatter-corrected image 710), corrected using the herein described scatter correction method (box grid infill, second scatter-corrected image 720), and corrected using tailing scatter correction (no infill, scatter and tailing corrected image 730). Hot spheres are the dark spots on the FIG. 7, which indicate regions of activity. Hot spheres are herein labeled by a respective diameter (e.g., Hot13 has a 13 mm diameter, Hot22 has a 22 mm diameter, etc.). As is shown in the graph 800, a contrast to noise ratio for each hot sphere is greatest for imaging where scatter and tailing correction is performed. The contrast to noise ratio may be an indicator of image quality, where image quality increases with a contrast percentage. The graph 800 thus shows that, of the hot spheres and methods for correction, image quality increases with an increasing sphere diameter and image quality is highest for the method of scatter and tailing correction described herein with respect to FIG. 5.

The method 500 is described herein with respect to the example of FIG. 4, where the photopeak 410 of Lu177 is corrected for scatter and tailing photons. Imaging data captured of Lu177 includes two scatter windows—the high scatter window 416 including scatter from the high peak 420 and the low scatter window 414 including scatter from the photopeak 410—and the peak window 412. The method 500 may also be applied to imaging data captured for studies which use a radionuclide that has less than two peaks and therefore may be divided into less than two scatter energy windows. Additionally, the method 500 may be applied to imaging data captured for studies with greater than two scatter energy windows. FIGS. 9 and 10 illustrate a set of images and corresponding contrast to noise ratio data for reconstruction of phantom data, wherein the phantom uses Tc99m radionuclide which may have a single scatter window below a photopeak window.

FIG. 9 shows a set of images 900 illustrating example corrected images with at least one of scatter correction and tailing correction according to conventional methods or an embodiment of the invention. Each of the set of images 900 are acquired of a same subject (e.g., a same phantom, such as the phantom 615 of FIG. 6) using a CZT detector, and are reconstructed with a same technique from a same energy window (e.g., a Tc99m peak). In the set of images 900, white regions illustrate regions with no activity while shaded regions indicate regions with activity.

In particular, the set of images 900 includes a first scatter-corrected image 910 which is reconstructed using a conventional scatter correction method. The set of images 900 also includes a second scatter-corrected image 920 which is reconstructed using reconstruction methods—as described with respect to operation 512 of the method 500. Compared to the first scatter-corrected image 910, the second scatter-corrected image 920 clearly shows a region of inactivity (white) as well as three regions of activity (black). Methods used to scatter correct the first scatter-corrected image 910 may be sufficient for scatter correcting data captured using a NaI detector, and are insufficient for scatter correcting data captured using a CZT detector, as shown in FIG. 9.

The set of images 900 further includes a scatter and tailing corrected image 930 which is reconstructed and corrected using methods described with respect to operation 516 of the method 500. Compared to the second scatter-corrected image 920, the scatter and tailing corrected image 930 clearly shows a region of inactivity (white) and three regions of activity (black). The scatter and tailing corrected image 930 additionally shows a fourth region of activity 912, and more clearly shows the region of inactivity, which may include two or more sub regions. A background of the scatter and tailing corrected image 930 has less noise compared to the second scatter-corrected image 920, due to the addition of tailing photons and thus an increase in statistics, which may enable visualization of the fourth region of activity 912 and detail of the region of inactivity. The scatter and tailing corrected image 930 is a more quantitatively accurate image, compared to the second scatter-corrected image 920 and the first scatter-corrected image 910.

FIG. 10 shows a graph 1000 illustrating example contrast to noise ratios of the set of images of FIG. 9. In particular, the graph 1000 depicts a contrast to noise ratio of each hot sphere of the phantom 615 for images reconstructed and corrected using conventional scatter correction (diagonal line infill, the first scatter-corrected image 910), corrected using the herein described scatter correction method (box grid infill, second scatter-corrected image 920), and corrected using tailing scatter correction (no infill, scatter and tailing corrected image 930). Hot spheres are the dark spots on the FIG. 9, which indicate regions of activity. Hot spheres are herein labeled by a respective diameter (e.g., Hot13 has a 13 mm diameter, Hot22 has a 22 mm diameter, etc.). As is shown in the graph 1000, a contrast to noise ratio for each hot sphere is greatest for imaging where scatter and tailing correction is performed. The contrast to noise ratio may be an indicator of image quality, where image quality increases with a contrast percentage. The graph 1000 thus shows that, of the hot spheres and methods for correction, image quality increases with an increasing sphere diameter and image quality is highest for the method of scatter and tailing correction described herein with respect to FIG. 5.

A technical effect of the disclosure includes an increased imaging data statistics and reduced noise in reconstructed images. This may result in increased image contrast to noise ratio (CNR) and/or reduce a radiation dose and/or scan time of an imaging scan, which may preserve the CNR. Additionally, systems and methods described herein may allow performance of more accurate scatter correction in imaging data having triple energy windows (e.g., photopeak window, high scatter energy window, low scatter energy window), thus increasing accuracy of image quantification.

As used herein, an element or step recited in the singular and preceded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first,"

"second," and "third," etc. are used merely as labels, and are not intended to impose numerical requirements or a particular positional order on their objects.

The disclosure also provides support for a method for scatter and tailing correction, comprising: acquiring imaging data with at least two energy windows, pre-processing acquired imaging data to separate distributions of scattered photons and peak photons, performing a main iterative reconstruction to reconstruct a corrected image using scatter correction, tailing correction, and/or scatter and tailing correction from distributions of scattered photons and peak photons, and outputting the corrected image. In a first example of the method, the at least two energy windows comprise a peak energy window and at least one scatter energy window with a range of energies less than and not overlapping with a range of energies of the peak energy window. In a second example of the method, optionally including the first example, pre-processing acquired imaging data includes performing an initial iterative reconstruction of images from each of the at least two energy windows to generate an initial peak image, and solving a system of equations to calculate a pure scatter image for each scatter energy window. In a third example of the method, optionally including one or both of the first and second examples, reconstructing the corrected image using scatter correction comprises eliminating scattered photons by: adding pre-calculated scatter from the pure scatter image for each scatter energy window to the initial peak image during each iteration of an iterative reconstruction to forward project a reconstructed, corrected image. In a fourth example of the method, optionally including one or more or each of the first through third examples, reconstructing the corrected image using tailing correction comprises eliminating scattered photons from the at least one scatter energy window, combining the at least one scatter energy window and the peak energy window into a single window, and adding tailing photons to the single window during iterative reconstruction to generate a tailing-corrected image. In a fifth example of the method, optionally including one or more or each of the first through fourth examples, reconstructing the corrected image using scatter and tailing correction comprises eliminating scattered photons from the at least one scatter energy window and from the peak energy window, combining the at least one scatter energy window and the peak energy window into a single window, and adding tailing photons to the single window during iterative reconstruction to generate a scatter and tailing-corrected image.

The disclosure also provides support for a system, comprising: a detector array including a plurality of detectors, and a computing device communicatively coupled to the detector array and configured with instructions in non-transitory memory that when executed cause the computing device to: acquire, via the detector array, imaging data separated into a photopeak energy window and at least one scatter energy window, remove photopeak photons from the imaging data in each of the at least one scatter energy window to obtain a corrected scatter distribution for each scatter energy window, correct the imaging data based on the corrected scatter distribution, and output a corrected image reconstructed from the corrected scatter distribution. In a first example of the system, the computing device is further configured with instructions in the non-transitory memory that when executed cause the computing device to: reconstruct a first photopeak image from the imaging data in the photopeak window with contrast and resolution matched to scattered photons, and reconstruct at least one scatter image from the imaging data of each of the at least one scatter energy window with contrast and resolution matched to the scattered photons. In a second example of the system, optionally including the first example, reconstructing the first photopeak image and the at least one scatter image with the contrast and the resolution matched to the scattered photons comprises performing iterative reconstruction of the imaging data in the photopeak energy window and the at least one scatter energy window, respectively, for a reduced number of iterations. In a third example of the system, optionally including one or both of the first and second examples, the plurality of detectors comprise CZT detectors. In a fourth example of the system, optionally including one or more or each of the first through third examples, the plurality of detectors comprise PET detectors with low energy resolution. In a fifth example of the system, optionally including one or more or each of the first through fourth examples, the system further comprises: a display communicatively coupled to the computing device, wherein the computing device outputs the corrected image to the display.

The disclosure also provides support for a method for nuclear medicine (NM) imaging, comprising: acquiring, with a plurality of detectors, imaging data separated into a photopeak energy window and a scatter energy window, reconstructing a first image including the photopeak energy window to generate a photopeak image, reconstructing an image of the scatter energy window to generate a scatter energy reconstructed image, performing at least one of scatter correction and/or tailing correction on the photopeak image, and outputting a corrected image. In a first example of the method, reconstructing the photopeak image comprises performing iterative reconstruction of the imaging data in the photopeak energy window for a number of iterations. In a second example of the method, optionally including the first example, the method further comprises: applying a Gaussian filter to imaging data of the scatter energy window. In a third example of the method, optionally including one or both of the first and second examples, correcting the scatter energy reconstructed image comprises separating the photopeak image from the scatter energy reconstructed image to obtain a pure scatter image. In a fourth example of the method, optionally including one or more or each of the first through third examples, performing scatter correction comprises eliminating imaging data of the pure scatter image from the photopeak image and performing iterative reconstruction of the photopeak image by adding weighted scatter to forward projections of the photopeak image. In a fifth example of the method, optionally including one or more or each of the first through fourth examples, performing tailing correction comprises adding imaging data of the photopeak image from the scatter energy window, performing iterative reconstruction of the summed energy windows and adding weighted pure scatter to forward projections of the image iteration. In a sixth example of the method, optionally including one or more or each of the first through fifth examples, the scatter energy window is a low scatter energy scatter window having an energy range less than the peak energy window. In a seventh example of the method, optionally including one or more or each of the first through sixth examples, the method further comprises: a second, high energy scatter window having an energy above the peak energy window.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for scatter and tailing correction, comprising:
   acquiring imaging data with at least two energy windows, wherein the at least two energy windows comprise a peak energy window and at least one scatter energy window with a range of energies less than and not overlapping with a range of energies of the peak energy window;
   pre-processing acquired imaging data to separate distributions of scattered photons and peak photons, wherein pre-processing acquired imaging data includes performing an initial iterative reconstruction of images from each of the at least two energy windows to generate an initial peak image, and solving a system of equations to calculate a pure scatter image for each scatter energy window;
   performing a main iterative reconstruction to reconstruct a corrected image using scatter correction, tailing correction, and/or scatter and tailing correction from distributions of scattered photons and peak photons, wherein reconstructing the corrected image using scatter correction comprises eliminating scattered photons by:
   adding pre-calculated scatter from the pure scatter image for each scatter energy window to the initial peak image during each iteration of an iterative reconstruction to forward project a reconstructed, corrected image; and
   outputting the corrected image.

2. The method of claim 1, wherein reconstructing the corrected image using tailing correction comprises eliminating scattered photons from the at least one scatter energy window, combining the at least one scatter energy window and the peak energy window into a single window, and adding tailing photons to the single window during iterative reconstruction to generate a tailing-corrected image.

3. The method of claim 1, wherein reconstructing the corrected image using scatter and tailing correction comprises eliminating scattered photons from the at least one scatter energy window and from the peak energy window, combining the at least one scatter energy window and the peak energy window into a single window, and adding tailing photons to the single window during iterative reconstruction to generate a scatter and tailing-corrected image.

4. A system, comprising:
   a detector array including a plurality of detectors; and
   a computing device communicatively coupled to the detector array and configured with instructions in non-transitory memory that when executed cause the computing device to:
   acquire, via the detector array, imaging data separated into a photopeak energy window and at least one scatter energy window;
   remove photopeak photons from the imaging data in each of the at least one scatter energy window to obtain a corrected scatter distribution for each scatter energy window;
   combine the at least one scatter energy window and the photopeak energy window into a single window;
   perform iterative reconstruction using the single window and the corrected scatter distribution to generate a corrected image, wherein performing iterative reconstruction comprises adding tailing photons to the single window during the iterative reconstruction; and output the corrected image.

5. The system of claim 4, wherein the computing device is further configured with instructions in the non-transitory memory that when executed cause the computing device to: reconstruct a first photopeak image from the imaging data in the photopeak window with contrast and resolution matched to scattered photons, and reconstruct at least one scatter image from the imaging data of each of the at least one scatter energy window with contrast and resolution matched to the scattered photons.

6. The system of claim 5, wherein reconstructing the first photopeak image and the at least one scatter image with the contrast and the resolution matched to the scattered photons comprises performing iterative reconstruction of the imaging data in the photopeak energy window and the at least one scatter energy window, respectively, for a reduced number of iterations.

7. The system of claim 4, wherein the plurality of detectors comprise CZT detectors.

8. The system of claim 4, wherein the plurality of detectors comprise PET detectors with low energy resolution.

9. The system of claim 4, further comprising a display communicatively coupled to the computing device, wherein the computing device outputs the corrected image to the display.

10. A method for nuclear medicine (NM) imaging, comprising:

acquiring, with a plurality of detectors, imaging data separated into a photopeak energy window and a scatter energy window;

reconstructing a first image including the photopeak energy window to generate a photopeak image;

reconstructing an image of the scatter energy window to generate a scatter energy reconstructed image;

performing at least one of tailing correction and scatter and tailing correction on the photopeak image; and outputting a corrected image.

11. The method of claim 10, wherein reconstructing the photopeak image comprises performing iterative reconstruction of the imaging data in the photopeak energy window for a number of iterations.

12. The method of claim 10, further comprising applying a Gaussian filter to imaging data of the scatter energy window.

13. The method of claim 10, wherein correcting the scatter energy reconstructed image comprises separating the photopeak image from the scatter energy reconstructed image to obtain a pure scatter image.

14. The method of claim 13, wherein performing scatter and tailing correction comprises eliminating imaging data of the pure scatter image from the photopeak image, combining the scatter energy window and the photopeak energy window into a single window, and performing iterative reconstruction of the single window by adding weighted pure scatter to forward projections of the image iteration.

15. The method of claim 10, wherein performing tailing correction comprises adding imaging data of the photopeak image from the scatter energy window, performing iterative reconstruction of the summed energy windows and adding weighted pure scatter to forward projections of the image iteration.

16. The method of claim 10, wherein the scatter energy window is a low scatter energy scatter window having an energy range less than the peak energy window.

17. The method of claim 16, further comprising a second, high energy scatter window having an energy above the peak energy window.

* * * * *